United States Patent
Elliott et al.

(10) Patent No.: US 6,649,759 B2
(45) Date of Patent: Nov. 18, 2003

(54) NEUROPEPTIDE Y ANTAGONISTS

(75) Inventors: Richard L. Elliott, East Lyme, CT (US); Robert M. Oliver, III, Gales Ferry, CT (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 10/225,663

(22) Filed: Aug. 21, 2002

(65) Prior Publication Data

US 2003/0100546 A1 May 29, 2003

Related U.S. Application Data

(63) Continuation of application No. 09/819,366, filed on Mar. 28, 2001, now abandoned.
(60) Provisional application No. 60/217,165, filed on Jul. 10, 2000, and provisional application No. 60/193,101, filed on Mar. 30, 2000.

(51) Int. Cl.⁷ ................ A61K 31/529; C07D 487/04
(52) U.S. Cl. ............... 544/281; 540/600; 514/217.06; 514/252.16; 514/259.3
(58) Field of Search ............... 544/281; 514/258, 514/252.16, 259.3, 217.06; 540/600

(56) References Cited

U.S. PATENT DOCUMENTS

| | | | | |
|---|---|---|---|---|
| 5,576,337 A | | 11/1996 | Bruns, Jr. et al. ........... | 514/324 |
| 5,688,949 A | * | 11/1997 | Inoue et al. ............... | 544/281 |
| 5,707,997 A | | 1/1998 | Shoji et al. ............... | 514/258 |
| 5,902,773 A | | 5/1999 | Benoit et al. .............. | 504/240 |
| 6,099,593 A | | 8/2000 | Terranova et al. ........... | 8/409 |

FOREIGN PATENT DOCUMENTS

| | | | |
|---|---|---|---|
| EP | 0347252 | 12/1989 | ......... A61K/31/505 |
| EP | 0369145 | 5/1990 | ......... C07D/487/14 |
| EP | 0434038 | 6/1991 | ......... C07D/471/04 |
| EP | 0646648 | 4/1995 | ......... C12P/21/00 |
| EP | 0759441 | 2/1997 | ......... C07K/14/47 |
| JP | 62010085 | 1/1987 | |
| JP | 03204877 | 9/1991 | |
| JP | 10101671 | 4/1998 | |
| JP | 10101672 | 4/1998 | |
| WO | WO9320078 | 10/1993 | ......... C07D/487/04 |
| WO | WO9415622 | 7/1994 | ......... A61K/31/70 |
| WO | WO9712615 | 4/1997 | ......... A61K/31/425 |
| WO | WO9743276 | 11/1997 | ......... C07D/401/06 |
| WO | WO9854093 | 12/1998 | ......... C01D/239/72 |

OTHER PUBLICATIONS

Grundemar and Hakanson, *TiPS*, May 1994 (vol. 15), pp 153–159.

* cited by examiner

Primary Examiner—Richard L. Raymond
(74) Attorney, Agent, or Firm—Peter C. Richardson; Gregg C. Benson; Arlene K. Musser

(57) ABSTRACT

Compounds of the formula

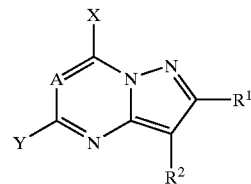

are neuropeptide Y antagonists and are effective in treating feeding disorders, cardiovascular diseases and other physiological disorders related to an excess of neuropeptide Y.

5 Claims, No Drawings

NEUROPEPTIDE Y ANTAGONISTS

This application is a continuation of U.S. patent application Ser. No. 09/819,366 filed on Mar. 28, 2001, now abandoned, which claims the benefit of U.S. Provisional Patent Application No. 60/217,165 filed Jul. 10, 2000 and U.S. Provisional Patent Application No. 60/193,101 filed Mar. 30, 2000, all of which are incorporated herein by reference in their entirety.

BACKGROUND OF INVENTION

1. Field of the Invention

This invention relates to the use of substituted pyrazolo pyrimidines and pyrazolo triazines which selectively bind to mammalian neuropeptide receptors. It further relates to the use of these compounds and compositions containing these compounds in treating conditions related to an excess of neuropeptide Y.

2. Description of the Related Art

Neuropeptide Y (NPY), a 36 amino acid peptide neurotransmitter, is a member of the pancreatic polypeptide class of neurotransmitters/neurohormones which has been shown to be present in both the periphery and central nervous system. NPY is one of the most potent orexogenic agents known and has been shown to play a major role in the regulation of food intake in animals, including humans. At least 6 NPY receptor subclasses have been identified and cloned to date, with two of the subclasses, NPY-1 and NPY-5, thought to be the most important receptor subtypes modulating food intake and energy expenditure. Hence, agents capable of blocking NPY binding at these receptor subtype(s) should have utility in a number of feeding disorders, including obesity, anorexia nervosa, bulimia nervosa; obesity-related disorder including but not limited to insulin resistance, diabetes, hyperlipidemia, and hypertension, as well as other indications for treatment where blockade of NPY activity is beneficial.

Grundemar and Hakanson. TiPS, May 1994 [Vol. 15], 153–159, state that, in animals, neuropeptide Y is a powerful stimulus of food intake, and an inducer of vasoconstriction leading to hypertension. They further point out that low levels of neuropeptide Y (NPY) are associated with loss of appetite. These reports clearly indicate that compounds that inhibit the activity of this protein will reduce hypertension and appetite in animals.

EP0759441 and U.S. Pat. No. 5,576,337 report that physiological disorders related to an excess of neuropeptide Y include:

disorders or diseases pertaining to the heart, blood vessels or the renal system, such as vasospasm, heart failure, shock, cardiac hypertrophy, increased blood pressure, angina, myocardial infarction, sudden cardiac death, arrythmia, peripheral vascular disease, and abnormal renal conditions such as impaired flow of fluid, abnormal mass transport, or renal failure; conditions related to increased sympathetic nerve activity for example, during or after coronary artery surgery, and operations and sugery in the gastrointestinal tract;

cerebral diseases and diseases related to the central nervous system, such as cerebral infarction, neurodegeneration, epilepsy, stroke, and conditions related to stroke, cerebral vasospasm and hemmorrhage, depression, anxiety, schizophrenia, and dementia;

conditions related to pain or nociception;

diseases related to abnormal gastrointenstinal motility and secretion, such as different forms of ileus, urinary incontinence, and Crohn's disease;

abnormal drink and food intake disorders, such as anorexia and metabolic disorders;

diseases related to sexual dysfunction and reproductive disorders;

conditions or disorders associated with inflammation;

respiratory diseases, such as asthma and conditions related to asthma and bronchoconstriction; and diseases related to abnormal hormone release, such as leutinizing hormone, growth hormone, insulin, and prolactin.

A patent application WO 9535298 entitled "Preparation and formulation of pyrazolopyrimidine derivatives as analgesics" [Shoji, Yasuo; Inoue, Makoto; Okamura, Takashi; Hashimoto, Kinji; Ohara, Masayuki; Yasuda, Tsuneo. (Otsuka Pharmaceutical Factory, Inc., Japan). PCT Int. Appl. 89 pp.] as well as JP 10101672 [Adenosine reinforcement agents. Moritoki, Hideki; Iwamoto, Takeshi; Yasuda, Tsuneo. (Otsuka Pharmaceutical Co., Ltd., Japan). Jpn. Kokai Tokkyo Koho 22 pp.] and JP 10101671 [Nitrogen monooxide synthase inhibitors. Moritoki, Hideki; Iwamoto, Takeshi; Yasuda, Tsuneo; 25 pp.]claim a series of aminopyrazolopyrimidines of the formula

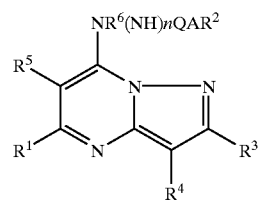

where $R^1$ represents hydrogen, lower alkyl, cycloalkyl, thienyl, furyl, lower alkenyl or phenyl; $R^2$ represents naphthyl, cycloalkyl, furyl, thienyl, pyridyl, phenoxy or phenyl; $R^3$ represents hydrogen, Ph or lower alkyl; $R^4$ represents hydrogen, lower alkyl, lower alkoxycarbonyl, phenyl-substituted lower alkyl, Ph or halogen; $R^5$ represents hydrogen or lower alkyl; $R^6$ represents hydrogen, lower alkyl, phenyl-substituted lower alkyl or benzoyl; Q represents carbonyl or sulfonyl; A represents a single bond, lower alkylene or lower alkenylene; and n represents 0 or 1.

WO 9218504 [Preparation of pyrazolo[1,5-a]pyrimidine derivatives antiinflammatory agents. Inoue, Makoto; Hashimoto, Kinji; Kuwahara, Toshiko; Sugimoto, Yukio; Uesako, Takuji; Funato, Toshiaki. 48 pp.] and JP 03204877 [Preparation of pyrazolo[1,5-a]pyrimidine derivatives as drugs. Inoue, Makoto; Hashimoto, Kinji.; 10 pp.] describe compounds of the formula:

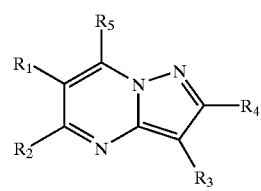

where $R^1$—$R^4$ may be hydrogen, carboxyl, lower alkoxycarbonyl, phenyl, or lower alkyl or cycloalkyl which may be each substituted with hydroxy, carboxyl or lower alkoxycarbonyl, or alternatively $R^1$ and $R^2$ may combined together to form lower alkylene; $R^5$ represents —$SR^6$ or —$NR^7R^8$; and $R^7$ and $R^8$ represent each hydrogen or phenyl which may be substituted with one to three groups, or $R^7$ and $R^8$ may be combined to form, together with the nitrogen atom to which they are bound, 1-pyrrolidinyl, 2-oxo-1-pyrrolidinyl, or 1-piperazinyl which may be substituted with hydroxy-lower alkyl or diphenyl-lower alkyl.

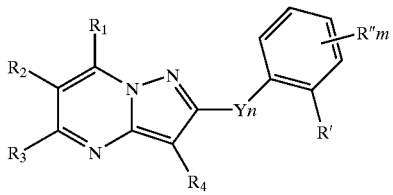

The patent WO 9635690 A1 [Pyrazolo[1,5-a]pyrimidines, process for preparing them, and their use as as pesticides and fungicides. Benoit, Remy; Grote, Thomas; Bayer, Herbert; Mueller, Bernd; Oberdorf, Klaus; Sauter, Hubert; Ammermann, Eberhard; Lorenz, Gisela; Strathmann, Siegfried). 115 pp.] covers compound of the general structure below where n=0 or 1; Y=O, S, $NH_2$, $OCH_2$, $SCH_2$, $NH_2CH_2$, $CH_2O$, $CH_2S$, $CH_2NH_2$, $CH_2CH_2$, $CH_2$:Rb, or C.tplbond.C; and R'=C(:CHOMe)$CO_2$Me, C(:CHOMe)CONHMe, C(:NOMe)$CO_2$Me, C(:NOCH$_3$)CONHMe, C(:NOMe)CONH$_2$, C(:NOMe)$CO_2$H, C(:CHMe)$CO_2$Me, C(:CHEt)$CO_2$Me, C(:CHOMe)COMe, C(:NOMe)COMe, C(:NOMe)COEt, N(OMe)$CO_2$Me, N(Me)$CO_2$Me, N(Et)$CO_2$Me, C(:NOMe)R where R=2-oxazolyl, 1,3,4-oxadiazol-2-yl, 1,2,4-oxadiazol-5-yl, 1,2,4-oxadiazol-3-yl.

Patents EP 347252 [Preparation of triazolo- and pyrazolopyrrolopyrimidines, their use in cacexia treatment, and formulations containing them. Takiguchi, Yo; Ohsumi, Jun; Shimoji, Yasuo; Sasagawa, Kazuhiko. (Sankyo Co., Ltd., Japan) 45 pp] and EP 508549 [New triazolo-pyrimidine and pyrazolo-pyrimidine derivs. for treating cachexia, e.g. 8-benzyl-7,8-dihydro-5-methyl-6H-pyrazole-(1,5A)-pyrrolo-(3,2E)-pyrimidine. Ohsumi, J; Sasagawa, K; Shimoji, Y; Takiguchi, Y. (Sankyo Co., Ltd., Japan) 39 pp] describe compounds of the formula below where Y can be N or $CR^2$ and $R^1$ can be, among other things, substituted alkyl or aryl; $R^2$ is H or halogen; $R^3$ is alkyl or cycloalkyl; $R^4$ and $R^5$ is hydrogen (when dashed line represent single bond) or hydrogen or halogen (when dashed line represents double bond) and $R^6$ is H, alkyl, alkenyl, alkynyl, cycloalkyl, aryl, or alkaryl.

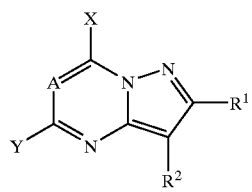

Likewise, EP 369145 [Preparation of pyrrolo[3,2-e]pyrazolo[1,5-a]pyrimidines as cardiovascular agents and bronchodilators. Tsujitani, Michihiko; Kishii, Kenichi; Inazu, Masato; Morimoto, Toshihiro; Motoki, Yoshiaki; Matsuo, Ichiro. (Pola Chemical Industries, Inc., Japan). 20 pp.] covers structures of the type I below where $R^1$ and $R^2$ can be, among other things, H, alkyl, cycloalkyl, phenyl, or a heterocyclic group and $R^3$ is H or CN.

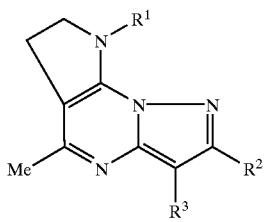

SUMMARY OF THE INVENTION

This invention provides compounds of the formula:

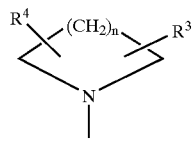

Wherein: A is —CH=; or —N=; or —CR=; X is

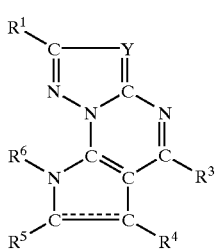

$R^1$ is phenyl, thienyl or pyridyl each optionally substituted with one to three substituents selected from halogen, —$OCF_3$, $NO_2$, CN, hydroxy, alkylalkoxy, COOH, $C_1$–$C_6$alkyl, $C_1$–$C_6$hydroxyalkyl, $C_1$–$C_6$ aminoalkyl, aryl, heteroaryl, alkoxy, acyloxy, $NR^7R^8$, $C_1$–$C_4$alkylthio, mono-, di-, or trihaloalkyl; or

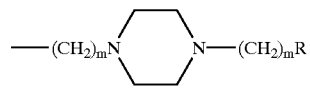

wherein;
R is phenyl, substituted phenyl, heteroaryl, $C_1$–$C_6$alkyl, hydrogen, OH, or alkoxy;
$R^2$ is hydrogen or $C_1$–$C_6$alkyl;
$R^3$ and $R^4$ are independently hydrogen, hydroxyl, —N($C_1$–$C_3$alkyl)$_2$, $C_1$–$C_6$alkyl, nitro, cyano, alkylalkoxy, or aryloxy;
Y is hydrogen, $C_1$–$C_6$alkyl, or pyridyl; n is 1 to 3; and m is 1 to 3; $R^7$ and $R^8$ are H or $C_1$–$C_6$ alkyl;
and with the proviso that if $R^1$ is phenyl, $R^2$ is hydrogen and Y is methyl; X must not be 1-pyrrolidine.

In another aspect, this invention comprises a compound of formula I wherein:
A is —CH=;
n is 0 to 3;
$R^3$ is —H or —$CH_3$;
$R^4$ is —H;
Y is methyl;
$R^2$ is hydrogen; and
$R^1$ is 3-chlorophenyl, 4-chlorophenyl or thienyl.

In another aspect, this invention comprises a compound of Formula I wherein:

A is —CH;
Y is methyl;
n is 2;
$R^3$ and $R^4$ are H;
$R^1$ is halogenated phenyl, or trifluoromethoxyphenyl; and $R^2$ is hydrogen.

In another aspect, this invention comprises a method of inhibiting or alleviating a pathological condition or physiological disorder in a mammal characterized by an excess of neuropeptide Y which comprises administering to a mammal in need of such treatment a neuropeptide Y inhibiting amount of the compound of Formula I,

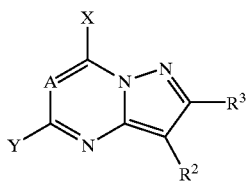

(I)

wherein A is —CH=; —CR=; or —N=;
X is $NR^4R^5$ where $R^4$ and $R^5$ are selected independently from $C_1$–$C_8$ alkyl, $C_2$–$C_8$ alkenyl, $C_3$–$C_8$ cycloalkyl, $C_5$–$C_8$ cycloalkenyl, $C_2$–$C_8$ alkynyl, $C_2$–$C_8$ alkylalkoxy, alkylaryl, alkylheteroaryl, $SO_2R^7$, or $SO_2NR^7R^8$; each optionally substituted with 1–2 substituents independently selected from $R^6$; or $R^4$ and $R^5$ are taken together to be $C_3$–$C_8$ cycloalkyl, optionally substituted with 1–2 substituents independently selected from $R^6$; $C_5$–$C_8$ cycloalkenyl, optionally substituted with 1–2 substituents independently selected from $R^6$; or a heterocyclic ring containing up to two heteroatoms selected from the group consisting of —O—, —$NR^7$—, and —S(O)m-, optionally substituted with 1–3 substituents independently selected from $R^6$; when $R^4$ and $R^5$ are taken together to be $C_3$–$C_8$ cycloalkyl, $C_5$–$C_8$ cycloalkenyl, or a heterocyclic ring as described above then said ring system may be further substituted to form an additional 3–8 membered ring optionally containing up to two heteroatoms selected from the group consisting of —O—, —$NR^7$—, and —S(O)m- (m=0–2); $R^5$ may be selected from $NR^7R^8$;

$R^6$ is selected independently from hydrogen; halogen, nitro, cyano, hydroxy, alkylalkoxy, COOH, $C_1$–$C_6$ alkyl; $C_1$–$C_6$ hydroxyalkyl, $C_1$–$C_6$ aminoalkyl, aryl, heteroaryl, aryloxy, heteroaryloxy, alkoxy; acyloxy, $NR^7NR^8$, $C_1$–$C_4$ alkylthio, mono-, di-, or trihaloalkyl;

$R^7$ and $R^8$ are independently selected from H, $C_1$–$C_6$ alkyl; $C_2$–$C_6$ alkenyl, alkylalkoxy, $C_2$–$C_6$ alkynyl, aryl, or heteroaryl; and may be joined to form a carbocyclic or heterocyclic ring;

$R^1$ is selected from H, $C_1$–$C_8$ alkyl, $C_2$–$C_8$ alkenyl, $C_3$–$C_8$ cycloalkyl, $C_5$–$C_8$ cycloalkenyl, or $C_2$–$C_8$ alkynyl, or alkylalkoxy, or $R^1$ and X may be joined together to form a 5–8 membered nitrogen-containing ring optionally containing an additional heteroatom selected from the group consisting of —O—, —$NR^7$—, and —S(O)m- and said 5–8 membered ring optionally substituted with 1–2 substituents chosen from $R^6$; said 5–8 membered ring may also contain a carbonyl group; $R^1$ and Y may be joined together to form a 5–8 membered ring optionally containing a heteroatom selected from the group consisting of —O—, —$NR^7$—, and —S(O)m- and said 5–8 membered ring optionally substituted with 1–2 substituents chosen from $R^6$, as well as said 5–8 membered ring containing a carbonyl group;

Y is selected from $C_1$–$C_6$ alkyl; alkoxyalkyl, $C_2$–$C_6$ -alkenyl; $C_2$–$C_6$ -alkynyl, alkoxy, aryl, or heteroaryl, or $NR^4R^5$ as defined for X;

n is 0 to 3;

$R^3$ is selected from aryl or heteroaryl optionally substituted with 1–3 substituents chosen from $R^6$.

The skilled chemist will be aware that some compounds of formula I may exist in tautomeric forms which are isomers differing in the relative position of a hydrogen atom. All such tautomers and mixtures thereof are included in this invention.

This invention also comprises a method of treating a pathological condition in a mammal characterized by an excess of neuropeptide Y wherein said pathological condition or physiological disorder is a feeding disorder selected from obesity or bulimia.

In another aspect, this invention comprises a method of inhibiting or alleviating a pathological condition or physiological disorder in a mammal wherein said pathological condition or physiological disorder is selected from the group consisting of: disorders or diseases pertaining to the heart, blood vessels or the renal system, such as vasospasm, heart failure, shock, cardiac hypertrophy, increased blood pressure, angina, myocardial infarction, sudden cardiac death, arrythmia, peripheral vascular disease, and abnormal renal conditions such as impaired flow of fluid, abnormal mass transport, or renal failure;

conditions related to increased sympathetic nerve activity for example, during or after coronary artery surgery, and operations and surgery in the gastrointestinal tract;

cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, and dementia;

conditions related to pain or nociception;

diseases related to abnormal gastrointenstinal motility and secretion, such as different forms of ileus, urinary incontinence, and Crohn's disease;

abnormal drink and food intake disorders, such as anorexia and metabolic disorders;

diseases related to sexual dysfunction and reproductive disorders;

conditions or disorders associated with inflammation;

respiratory diseases, such as asthma and conditions related to asthma and bronchoconstriction; and diseases related to abnormal hormone release, such as leutinizing hormone, growth hormone, insulin, and prolactin.

This invention provides a method of inhibiting or alleviating a pathological condition in a mammal characterized by an excess of neuropeptide Y wherein said mammal is a dog or cat.

This invention also includes a pharmaceutical composition for inhibiting or alleviating a pathological condition or physiological disorder in a mammal characterized by or associated with an excess of neuropeptide Y, which comprises a compound of formula I or a pharmaceutically acceptable salt thereof and a pharmaceutically acceptable carrier.

The subject invention also includes isotopically-labelled compounds, which are identical to those recited in Formulae I and II but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, 18O, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

In another aspect, this invention provides a compound selected from the group consisting of:

7-Pyrrolidin-1-yl-5-methyl-2-phenyl-pyrazolo[1,5-a] pyrimidine;
7-Azetidin-1-yl-5-methyl-2-phenyl-pyrazolo[1,5-a] pyrimidine;
5-Isopropyl-2-phenyl-7-pyrrolidin-1-yl-pyrazolo[1,5-a] pyrimidine;
5-Ethyl-2-phenyl-7-pyrrolidin-1-yl-pyrazolo[1,5-a] pyrimidine;
2-Phenyl-5-pyridin-2-yl-7-pyrrolidin-1-yl-pyrazolo[1,5-a] pyrimidine;
5-Methyl-7-pyrrolidin-1-yl-2-thiophen-2-yl-pyrazolo[1,5-a] pyrimidine;
2-(3-Chloro-phenyl)-5-methyl-7-pyrrolidin-1-yl-pyrazolo[1,5-a]pyrimidine;
2-(4-Chloro-phenyl)-5-methyl-7-pyrrolidin-1-yl-pyrazolo[1,5-a]pyrimidine;
5-Methyl-7-pyrrolidin-1-yl-2-(4-trifluoromethoxy-phenyl)-pyrazolo[1,5-a]pyrimidine;
2,5-Diphenyl-7-pyrrolidin-1-yl-pyrazolo[1,5-a]pyrimidine;
[4-(5-Methyl-7-pyrrolidin-1-yl-pyrazolo[1,5-a]pyrimidin-2-yl)-phenyl]-methanol;
2-(4-Chloro-phenyl)-5-methyl-7-(2-methyl-pyrrolidin-1-yl)-pyrazolo[1,5-a]pyrimidine;
2-(4-Chloro-phenyl)-5-methyl-7-piperidin-1-yl-pyrazolo[1,5-a]pyrimidine;
{1(S)-[2-(4-Chloro-phenyl)-5-methyl-pyrazolo[1,5-a]pyrimidin-7-yl]-pyrrolidin-3-yl}-dimethyl-amine;
{1(R)-[2-(4-Chloro-phenyl)-5-methyl-pyrazolo[1,5-a]pyrimidin-7-yl]-pyrrolidin-3-yl}-dimethyl-amine;
2-(4-Chloro-phenyl)-5-methyl-7-(2-methyl-piperidin-1-yl)-pyrazolo[1,5-a]pyrimidine;
1-[2-(4-Chloro-phenyl)-5-methyl-pyrazolo[1,5-a]pyrimidin-7-yl]-pyrrolidin-3-ol;
2-[4-(4-Ethyl-piperazin-1-ylmethyl)-phenyl]-5-methyl-7-pyrrolidin-1-yl-pyrazolo[1,5-a]pyrimidine;
Benzyl-[4-(5-methyl-7-pyrrolidin-1-yl-pyrazolo[1,5-a]pyrimidin-2-yl)-benzyl]-amine; and
5-Methyl-2-pyridin-4-yl-7-pyrrolidin-1-yl-pyrazolo[1,5-a]pyrimidine.

DETAILED DESCRIPTION OF THE INVENTION

The term "pharmaceutically acceptable salt(s)", as used herein, unless otherwise indicated, includes salts of acidic or basic groups that may be present in the compounds of formula I. For example, pharmaceutically acceptable salts include sodium, calcium and potassium salts of carboxylic acid groups and hydrochloride salts of amino groups. Other pharmaceutically acceptable salts of amino groups are hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts. The preparation of such salts is described below.

The compounds of the present invention may have asymmetric carbon atoms. Diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

The compounds of formula I that are basic in nature are capable of forming a wide variety of different salts with various inorganic and organic acids. Although such salts must be pharmaceutically acceptable for administration to animals, it is often desirable in practice to initially isolate the compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula I that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before.

In either case, stoichiometric quantities of reagents are preferably employed in order to ensure completeness of reaction and maximum yields of the desired final product.

As used herein, the term "alkyl" means a straight or branched saturated carbon chain of the specified number of carbon atoms. "Cycloalkyl" means a carbocyclic ring of the designated number of carbon atoms. Each cycloalkyl ring may be optionally substituted with one to three R groups wherein R is $C_1$–$C_6$ alkyl.

"Halogen" means F, Cl, Br or I.

The preparation of compounds of Formula I of the present invention may be carried out in sequential or convergent synthetic routes. Syntheses describing the preparation of the compounds of the invention are shown in the following Schemes. The skills required for carrying out the reaction and purification of the resulting products are known to those in the art. Purification procedures include crystallization and normal phase or reverse phase chromatography.

5-a]pyrimidines of the formula (III). Subsequent conversion of the hydroxy compound to the 7-chloro compound (IV) using a chlorinating reagent such as $POCl_3$, followed by displacement of the chlorine by a nitrogen nucleophile affords 7-amino pyrazolo[1,5-a]pyrimidines of the general structure (I). Similarly, condensation of a malonate diester (Y=OR for (II)) with an aminopyrazole (I), follow by bis-chlorination affords the dichloride (IV; Y=Cl). Further nucleophilic displacements affords compounds of the type (I) where Y can be N or O.

Scheme 2
Preparation of pyrazolo[1,5-a][1,3,5]triazines of the Formula (II).

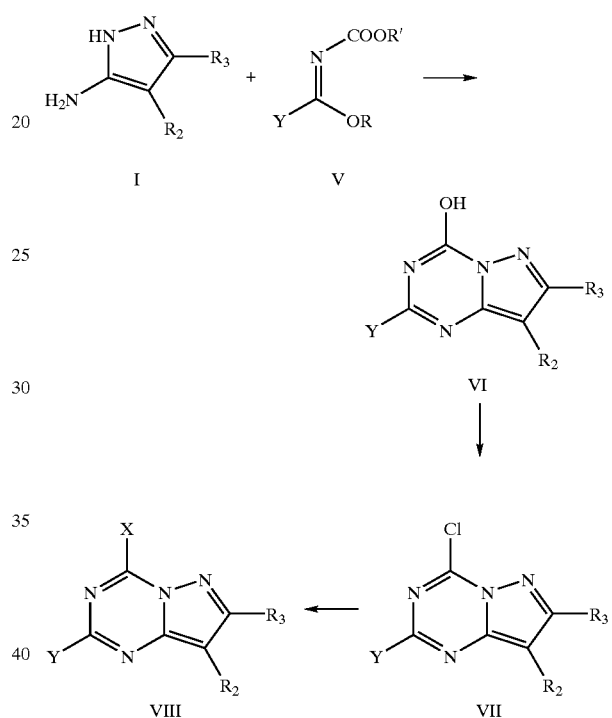

Scheme 1
Preparation of pyrazolo[1,5-a]pyrimidines of the Formula (I)

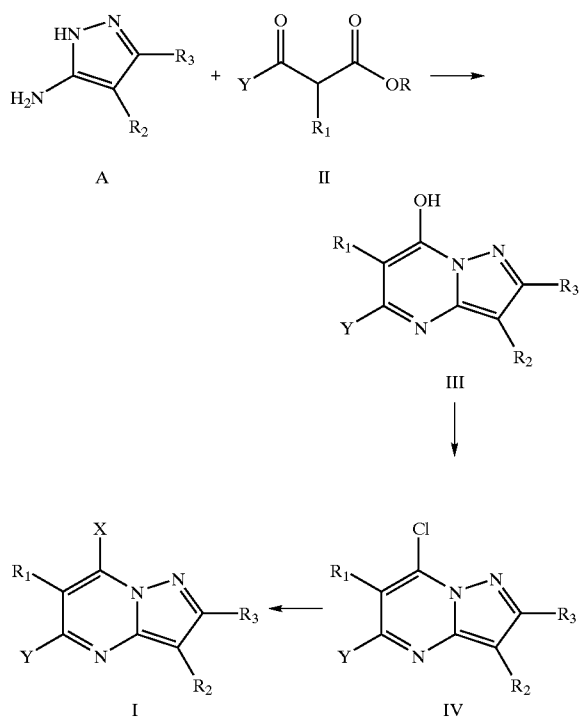

Condensation of an 3-aminopyrazole (A) with a beta-keto ester (Y=carbon) of the type (II) under dehydrating conditions (e.g. refluxing AcOH) affords 7-hydroxy pyrazolo[1, Condensation of an 3-aminopyrazole with an iminoether (Y=carbon) of the type (V) under dehydrating conditions (e.g. refluxing AcOH) affords compounds of the formula (VI). Subsequent conversion of the hydroxy compound to the 7-chloro compound (VII) using a chlorinating reagent such as $POCl_3$, followed by displacement of the chlorine by a nitrogen nucleophile affords compounds of the general structure VIII. An alternate synthetic scheme to afford pyrazolo[1,5-a][1,3,5]triazines is outline below.

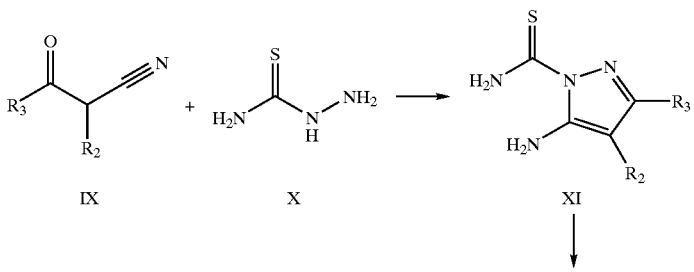

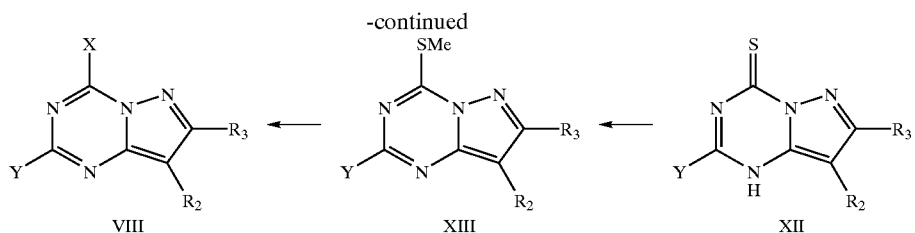

Condensation of a cyanoketone of the type (IX) with thiosemicarbazide (X) affords thiocarbamoyl aminopyrazoles of the formula (XI). Subsequent condensation with a carboxylic acid derivative or ortho ester affords compounds of the formula (XII) (Y=carbon), which can be alkylated to afford the S-alkyl derivative (XIII). Further displacement of the S-alkyl moiety by a nitrogen nucleophiles pyrazolo[1,5-a][1,3,5]triazines of the general structure (XIII).

EXAMPLES

Example 1 a). To a solution of 5-phenyl-2H-pyrazol-3-ylamine (9.18 g, 57.6 mmol) and 3-oxo-butyric acid methyl ester (9.33 mL, 86.5 mmol) in acetic acid (70 ml) was refluxed for 28 hrs. The reaction mixture was then allowed to cool, filtered, and the precipitated solid washed with acetic acid and dried in vacuo to afford 5-methyl-2-phenyl-pyrazolo[1,5-a]pyrimidin-7-ol as a white solid (11.86 g; 85%) MS m/z @ 242 (m+1).

b). A solution of 5-methyl-2-phenyl-pyrazolo[1,5-a]pyrimidin-7-ol (4.0 g, 17.76 mmoles) and $POCl_3$ (20 mL, excess) was refluxed for 1 hr. The reaction mixture was then allowed to cool and the excess $POCl_3$ removed in vacuo to afford crude 7-chloro-5-methyl-2-phenyl-pyrazolo[1,5-a]pyrimidine as a red solid. Chromatographic purification (silica; $CH_2Cl_2$, then 10% $MeOH/CH_2Cl_2$ afford the product as a red solid (3.8 g; 88% yield). MS m/z @ 244/246 (m+1).

c). A solution of 7-chloro-5-methyl-2-phenyl-pyrazolo[1,5-a]pyrimidine (272 mg, 1.12 mmoles) and pyrrolidine (0.373 mL, 4.46 mmol) in ethanol (10 mL) was refluxed for 18 hrs, then the volatiles removed in vacuo, EtOAc added, and the organic layer washed with sat. aq. sodium bicarbonate, water, and brine, then dried ($Na_2SO_4$) to afford the crude product. Chromatographic purification (silica; 50% EtOAc/Hex, afforded the product (34 mg, 11% yield). MS m/z @ 279 (m+1).

Example 2

The reaction to obtain the product of example 2 was run similarly to that described in step c of example 1, substituting azetidine for pyrrolidine, and using N-methyl pyrrolidinone as a solvent rather than ethanol, as well as 3.0 equiv. $Et_3N$; to afford, after chromatographic purification, 5.3 mg product (13%). MS m/z @ 265 (m+1).

Example 3

The reactions used to obtain the product of example 3 were run similarly to that described in example 1, substituting 4-methyl-3-oxo-pentanoic acid ethyl ester for methyl acetoacetate in step a, and performing step b using $POCl_3$ in the presence of N,N-dimethylaniline. MS m/z @ 307 (m+1).

Example 4

The reactions used to obtain the product of example 4 were run similarly to that described in example 1, substituting 3-oxo-pentanoic acid ethyl ester for methyl acetoacetate in step a, and performing step b using $POCl_3$ in the presence of N,N-dimethylaniline. MS m/z @ 293 (m+1).

Example 5

The reactions used to obtain the product of example 5 were run similarly to that described in example 1, substituting 3-oxo-3-pyridin-2-yl-propionic acid ethyl ester for methyl acetoacetate in step a, and performing step b using $POCl_3$ in the presence of N,N-dimethylaniline. MS m/z @ 289 (m+1).

Example 6

The reactions used to obtain the product of example 6 were run similarly to that described in example 1, substituting 5-thiophen-2-yl-2H-pyrazol-3-ylamine for 5-phenyl-2H-pyrazol-3-ylamine in step a, and performing step b using $POCl_3$ in the presence of N,N-dimethylaniline. MS m/z @ 289 (m+1).

Example 7

The reactions used to obtain the product of example 7 were run similarly to that described in example 1, substituting 5-(3-chloro-phenyl)-2H-pyrazol-3-ylamine for 5-phenyl-2H-pyrazol-3-ylamine in step a, and performing step b using $POCl_3$ in the presence of N,N-dimethylaniline. MS m/z @ 314 (m+1).

Example 8

The reactions used to obtain the product of example 8 were run similarly to that described in example 1, substituting 5-(4Chloro-phenyl)-2H-pyrazol-3-ylamine for 5-phenyl-2H-pyrazol-3-ylamine in step a, and performing step b using $POCl_3$ in the presence of N,N-dimethylaniline. MS m/z @ 314 (m+1).

Example 9

The reactions used to obtain the product of example 9 were run similarly to that described in example 1, substituting 5-(4-trifluoromethoxy-phenyl)-2H-pyrazol-3-ylamine for 5-phenyl-2H-pyrazol-3-ylamine in step a, and performing step b using $POCl_3$ in the presence of N,N-dimethylaniline. MS m/z @ 364 (m+1).

Example 10

The reactions used to obtain the product of example 10 were run similarly to that described in example 1, substituting 3-oxo-3-phenyl-propionic acid ethyl ester for methyl acetoacetate in step a, and performing step b using $POCl_3$ in the presence of N,N-dimethylaniline. MS m/z @ 341 (m+1).

Example 11

The reactions used to obtain the product of example 11 were run similarly to that described in example 1, substituting 4-(5-amino-1H-pyrazol-3-yl)-benzoic acid methyl ester for 5-phenyl-2H-pyrazol-3-ylamine in step a, performing step b using $POCl_3$ in the presence of N,N-dimethylaniline, and after performing step C [to obtain 4-(5-methyl-7-pyrrolidin-1-yl-pyrazolo[1,5-a]pyrimidin-2-yl)-benzoic acid methyl ester] reducing the ester funtionality to the hydroxymethyl group as follows. A solution of 4-(5-methyl-7-pyrrolidin-1-yl-pyrazolo[1,5-a]pyrimidin-2-yl)-benzoic acid methyl ester (0.19 mmoles) in THF (5 ml) was cooled to 0° C. and diisobutyl aluminum hydride (0.5mmol, 1.0M solution in hexanes) was added. The reaction stirred under ice-cooling for 30 minutes, then the THF was concentrated under reduced pressure and the residue dissolved in dichloromethane. The organic phase was washed with saturated sodium bicarbonate solution, and the organic phase dried with magnesium sulfate, filtered and concentrated. Chromatographic purification (silica, 20% EtOAc/hexane) afforded desired product (50 mg, 84.4% yield). MS m/z @ 309(m+1).

Example 12

The reactions used to obtain the product of example 12 were run similarly to that described in example 1, substituting 2-methylpyrrolidine for pyrrolidine. MS m/z @ 327/329 (m+1/m+3).

Example 13

The reactions used to obtain the product of example 13 were run similarly to that described in example 1, substituting piperidine for pyrrolidine. MS m/z @ 327/329 (m+1/m+3).

Example 14

The reactions used to obtain the product of example 14 were run similarly to that described in example 1, substituting 3(S)-dimethylaminopyrrolidine for pyrrolidine. MS m/z @ 356/358 (m+1/m+3).

Example 15

The reactions used to obtain the product of example 15 were run similarly to that described in example 1, substituting 3(R)-dimethylaminopyrrolidine for pyrrolidine. MS m/z @ 356/358 (m+1/m+3).

Example 16

The reactions used to obtain the product of example 16 were run similarly to that described in example 1, substituting 2-methylpiperidine for pyrrolidine. MS m/z @ 341/343 (m+1/m+3).

Example 17

The reactions used to obtain the product of example 17 were run similarly to that described in example 1, substituting 3(R)-hydroxypyrrolidine for pyrrolidine. MS m/z @ 329/331 (m+1/m+3).

Example 18

To a solution of 4-(7-chloro-5-methyl-pyrazolo[1,5-a]pyrimidin-2-yl)-benzoic acid methyl ester (15.1 mmol) in 1-methyl-2-pyrrolidinone (50 ml) was added pyrrolidine (151 mmol) and the reaction heated at 80° C. for 72 hours. The resultant solid precipitate was filtered and dried under vacuum, then dissolved in 10% NaOH and the aqueous phase washed with ethyl acetate, acidified with conc. HCl, and the resultant precipitated white solid filtered and dried under vacuum to afford 4-(5-Methyl-7-pyrrolidin-1-yl-pyrazolo[1,5-a]pyrimidin-2-yl)-benzoic acid. (3.9 g, 80% yield) MS m/z @323 (m+1).

This material (120 mg, 0.37 mmol) was then dissolved in $CH_2Cl_2$ (3 ml) and carbonyldiimidazole (70 mg, 0.41mmol) added and the reaction mixture stirred at room temperature for 2 h. N-Ethylpiperazine (40 mg, 0.38 mmol) was then added and the reaction mixture stirred for 12 h at room temperature. After stirring for 12 hours, additional N-ethylpiperazine (40 mg, 0.38 mmoles) was added and the reaction was stirred at room temperature for an additional 72 hours. The reaction mixture was then diluted with $CH_2Cl_2$ (20 ml) and the organic phase was washed with saturated sodium bicarbonate solution, dried ($MgSO_4$), and concentrated to afford, after chromatographic purification (silica gel, $CH_2Cl_2$) (4-ethyl-piperazin-1-yl)-[4-(5-methyl-7-pyrrolidin-1-yl-pyrazolo[1,5-a]pyrimidin-2-yl)-phenyl]-methanone (60 mg 38.5% yield) MS m/z @419.

This material (60 mg, 0.14 mmol) was dissolved in THF (4 ml) and $BH_3$-tetrahydrofuran complex (4 ml, 1.0M in THF) was then added. The reaction was heated at 80° C. for 16 h then quenched with 5% HCl solution for 20 minutes and the reaction mixture was made basic with NaOH. The reaction mixture was extracted with $CH_2Cl_2$ and the organic layer dried ($MgSO_4$) and concentrated. The resultant residue was dissolved in of ethanol (10 ml), $CsF_2$ (10 mg) was added, and the reaction was heated at 85° C. for 4 h. Ethanol was concentrated and product was extracted with $CH_2Cl_2$, and the organic phase was washed with saturated sodium bicarbonate solution, dried ($MgSO_4$), and concentrated to afford, after chromatographic purification (silica gel, $CH_2Cl_2$) 2-[4-(4-ethyl-piperazin-1-ylmethyl)-phenyl]-5-methyl-7-pyrrolidin-1-yl-pyrazolo[1,5-a]pyrimidine (4.8 mg, 10.0% yield) MS m/z @ 405 (m+1).

Example 19

The reactions used to obtain the product of example 19 were run similarly to that described in example 18, substituting benzylamine for ethylpiperazine. MS m/z @ 398 (m+1).

Example 20

The reactions used to obtain the product of example 20 were run similarly to that described in example 14, substituting 5-pyridin-4-yl-2H-pyrazol-3-ylamine for 5-(3-chlorophenyl)-2H-pyrazol-3-ylamine. MS m/z @ 280 (m+1).

NPY-5 Pyrazolopyrimidines with Binding Ki's <1000 nM

| Ex. | Structure | Mass Spec (M + 1) | Name |
|---|---|---|---|
| 1 | 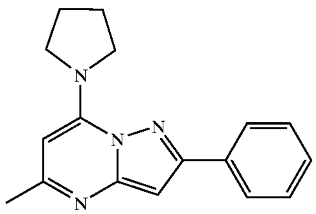 | 208 | 7-Pyrrolidin-1-yl-5-methyl-2-phenyl-pyrazolo[1,5-a]pyrimidine |
| 2 | 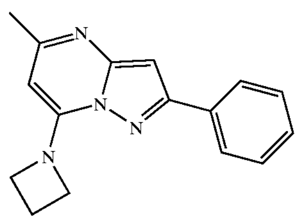 | 265 | 7-Azetidin-1-yl-5-methyl-2-phenyl-pyrazolo[1,5-a]pyrimidine |
| 3 | 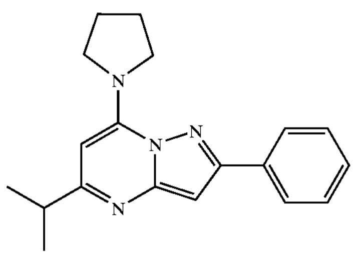 | 307 | 5-Isopropyl-2-phenyl-7-pyrrolidin-1-yl-pyrazolo[1,5-a]pyrimidine |
| 4 | 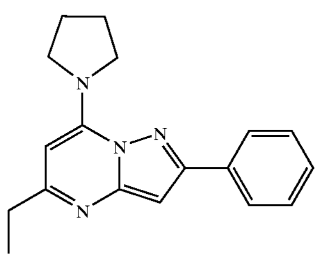 | 293 | 5-Ethyl-2-phenyl-7-pyrrolidin-1-yl-pyrazolo[1,5-a]pyrimidine |
| 5 | 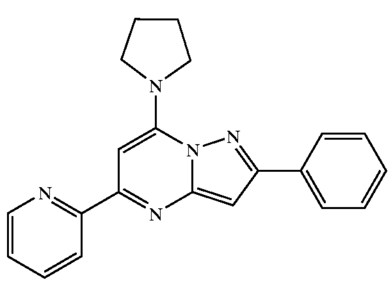 | 342 | 2-Phenyl-5-pyridin-2-yl-7-pyrrolidin-1-yl-pyrazolo[1,5-a]pyrimidine |
| 6 | 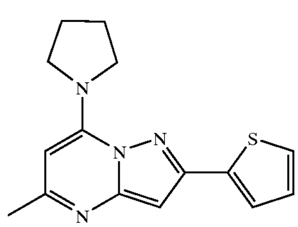 | 285 | 5-Methyl-7-pyrrolidin-1-yl-2-thiophen-2-yl-pyrazolo[1,5-a]pyrimidine |

-continued

NPY-5 Pyrazolopyrimidines with Binding Ki's <1000 nM

| Ex. | Structure | Mass Spec (M + 1) | Name |
|---|---|---|---|
| 7 | 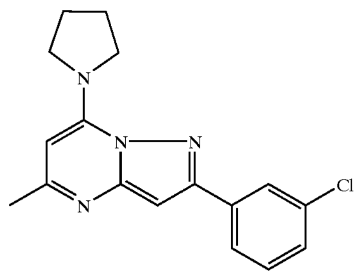 | 313 | 2-(3-Chloro-phenyl)-5-methyl-7-pyrrolidin-1-yl-pyrazolo[1,5-a]pyrimidine |
| 8 | 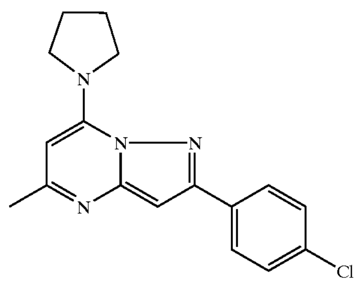 | 313 | 2-(4-Chloro-phenyl)-5-methyl-7-pyrrolidin-1-yl-pyrazolo[1,5-a]pyrimidine |
| 9 | 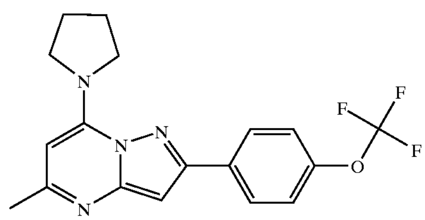 | 363 | 5-Methyl-7-pyrrolidin-1-yl-2-(4-trifluoromethoxy-phenyl)-pyrazolo[1,5-a]pyrimidine |
| 10 | 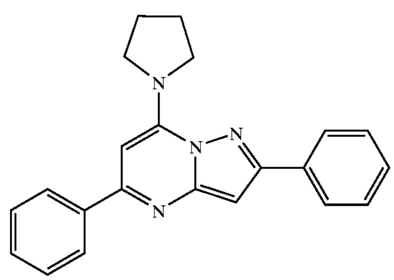 | 341 | 2,5-Diphenyl-7-pyrrolidin-1-yl-pyrazolo[1,5-a]pyrimidine |
| 11 | 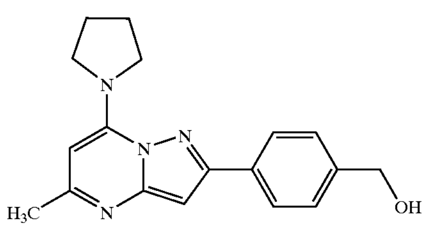 | 309 | [4-(5-Methyl-7-pyrrolidin-1-yl-pyrazolo[1,5-a]pyrimidin-2-yl)-phenyl]-methanol |
| 12 | 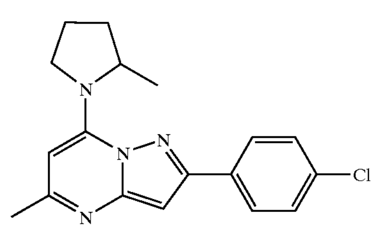 | 327/329 | 2-(4-Chloro-phenyl)-5-methyl-7-(2-methyl-pyrrolidin-1-yl)-pyrazolo[1,5-a]pyrimidine |

-continued

NPY-5 Pyrazolopyrimidines with Binding Ki's <1000 nM

| Ex. | Structure | Mass Spec (M + 1) | Name |
| --- | --- | --- | --- |
| 13 | 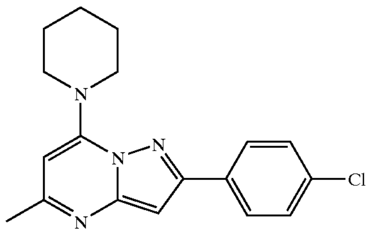 | 327/329 | 2-(4-Chloro-phenyl)-5-methyl-7-piperidin-1-yl-pyrazolo[1,5-a]pyrimidine |
| 14 | 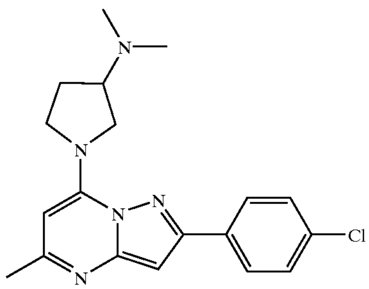 | 356/358 | {1(S)-[2-(4-Chloro-phenyl)-5-methyl-pyrazolo[1,5-a]pyrimidin-7-yl]-pyrrolidin-3-yl}-dimethyl-amine |
| 15 | 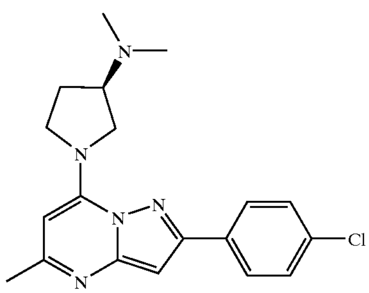 | 356/358 | {1(R)-[2-(4-Chloro-phenyl)-5-methyl-pyrazolo[1,5-a]pyrimidin-7-yl]-pyrrolidin-3-yl}-dimethyl-amine |
| 16 | 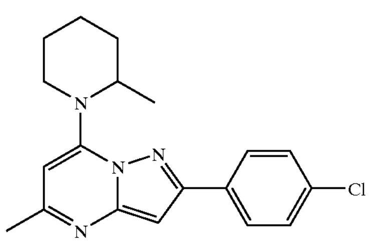 | 341/343 | 2-(4-Chloro-phenyl)-5-methyl-7-(2-methyl-piperidin-1-yl)-pyrazolo[1,5-a]pyrimidine |
| 17 | 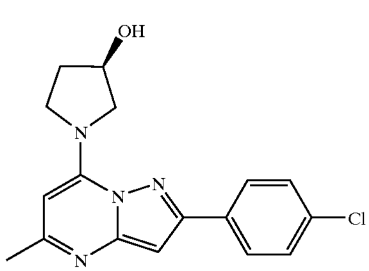 | 329/331 | 1-[2-(4-Chloro-phenyl)-5-methyl-pyrazolo[1,5-a]pyrimidin-7-yl]-pyrrolidin-3(R)-ol |

-continued

NPY-5 Pyrazolopyrimidines with Binding Ki's <1000 nM

| Ex. | Structure | Mass Spec (M + 1) | Name |
|-----|-----------|-------------------|------|
| 18 | 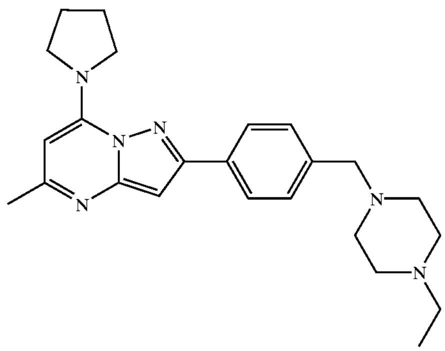 | 405 | 2-[4-(4-Ethyl-piperazin-1-ylmethyl)-phenyl]-5-methyl-7-pyrrolidin-1-yl-pyrazolo[1,5-a]pyrimidine |
| 19 | 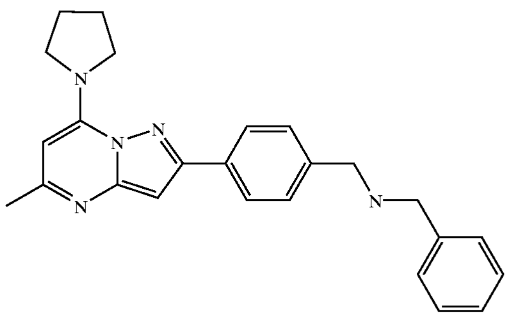 | 398 | Benzyl-[4-(5-methyl-7-pyrrolidin-1-yl-pyrazolo[1,5-a]pyrimidin-2-yl)-benzyl]-amine |
| 20 | 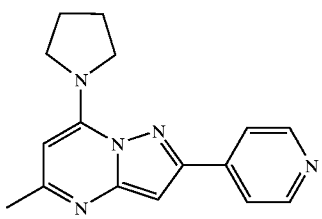 | 280 | 5-Methyl-2-pyridin-4-yl-7-pyrrolidin-1-yl-pyrazolo[1,5-a]pyrimidine |

Assay for NPY-5 Binding

[$^{125}$I]PYY Binding at Human NPY Receptors Expressed in Sf9 Cells

Baculovirus-infected Sf9 cells expressing recombinant human NPY 5 receptors are harvested at 48 hours. At the time of harvest, cell pellets are resuspended in lysis buffer (20 mM Tris-HCl, pH 7.4, 5 mM EDTA, 0.5 μg/ml leupeptin, 2 μg/ml Aprotonin and 200 mM PMSF) and homogenized using a Polytron (setting 3, 25–30 seconds). Homogenates are centrifuged at 4° C. for 5 minutes at 200×g (~1.5 rpm) to pellet the nuclei. The supernatant is collected into a fresh tube and centrifuged at 48,000×g for 10 minutes. Pellets are washed once in lysis buffer and centrifuged. The final pellet is resuspended in PBS and stored in aliquots at −80° C. Purified membranes are washed using PBS and resuspended in binding buffer (50 mM Tris(HCl), pH 7.4, 5 mM KCl, 120 mM NaCl, 2 mM CaCl$_2$, 1 mM MgCl$_2$, 0.1% bovine seurm albumin (BSA)). Membranes (20 μg/reaction tube) are added to polypropylene tubes containing 0.035 nM [$^{125}$I]PYY(porcine), displacers ranging from $10^{-12}$ M to $10^{-5}$ M, and buffer to yield a final volume of 0.5 mL. Nonspecific binding is determined in the presence of 1 μM NPY(human) and accounts for 10% of total binding. Following a 2 hour incubation at room temperature, the reaction is terminated by rapid vacuum filtration. Samples are filtered over presoaked GF/C Whatman filters (1.0% polyethylenemine) and rinsed 2 times with 5 mL cold binding buffer without BSA. A gamma counter is used to count filters with an efficiency of 85%. IC$_{50}$ values were calculated with the non-linear curve fitting program RS/1 (SigmaPlot, Jandel).

Functional Assay for NPY Receptors Expressed in Oocytes

Experiments were performed on Xenopus oocytes. Oocytes were prepared and maintained using standard protocols (Dascal and Lotan, in *Methods in Molecular Biology; Protocols in Molecular Neurobiology*, eds. Longstaff & Revest, Humana, Clifton, N.J., 13:1992). For the present experiments, oocytes were obtained from 6 frogs. Oocytes were recorded from 2–7 days following coinjection of GIRKI and the H17 NPY-1 or NPY-5 subtype mRNA (25 ng of each, 50 nL total volume).

Two electrode voltage clamp recordings were carried out using a Warner Instruments Oocyte clamp OC 725B. Data were collected on a Macintosh microcomputer and analyzed using Superscope software. Voltage and current electrodes were pulled from glass tubing (1.5 mM O.D.) on a Brown/Flaming micropipet puller (Sutter Instruments, model P-87). Electrodes contained 3M KCl and had resistances of 0.5–2 MOhms. Oocytes were bathed in normal external solution containing; 90 mM NaCl, 1 mM KCl, 1 mM $MgCl_2$, 1 mM $CaCl_2$, 5 mM HEPES, pH=7.4. Before NPY agonists or antagonists were introduced, a high $K^+$ solution containing; 1 mM NaCl, 90 mM KCl, 1 mM $MgCl_2$, 1 mM $CaCl_2$, 5 mM HEPES was applied to permit recording of the inwardly rectifying $K^+$ current. Drugs were applied diluted in the high $K^+$ media.

100 $\mu$M stocks of NPY, PP (pancreatic polypeptide) or NPY peptide fragments or PYY (peptide y) peptide fragments were prepared in water and frozen until needed.

Oocytes were voltage-clamped at −80 mV with two electrodes. Oocytes were initially superfused with normal external medium (approximate flow rate 4 ml/min.). Before drugs were applied, cells were superfused with high $K^+$ solution to permit activation of the inwardly rectifying $K^+$ current. In oocytes coinjected with NPY receptor and GIRK1 mRNA, the NPY agonist induced an additional inward current over the resting $K^+$ current caused by high $K^+$ medium. Because responses desensitized at slow, but varying rates, cumulative dose applications were administered to generate concentration response curves. Two to four doses of agonist were applied to each cell. Agonist dose responses in each cell were normalized against the response to a maximal concentration of human NPY. Dose response curves were fit with a logistic equation using Kaleidagraph software (Abelbeck software, Reading, Pa.).

The compound of formula I and pharmaceutically acceptable salts thereof (the active compound) may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. The active compound may be present in association with one or more non-toxic pharmaceutically acceptable carriers and/or diluents and/or adjuvants and if desired other active ingredients. The pharmaceutical compositions containing the active compound may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil liquid paraffin or olive oil.

Aqueous suspensions contain the active material in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally-occurring phosphatides, for example soy bean, lecithin, and esters or partial esters derived from fatty acids and hexitol anhydrides, for example sorbitan monoleate, and condensation products of the said partial esters with ethylene oxide, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The active compound may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

The active compound may be administered parenterally in a sterile medium, The drug, depending on the vehicle and concentration used can either be suspended or dissolved in the vehicle. Advantageously, adjuvants such as local anesthetics, preservatives and buffering agents can be dissolved in the vehicle.

Dosage levels of the order of from about 0.1 mg to about 15 mg of active compound per kilogram of body weight per day are useful in the treatment of the above-indicated conditions (about 7 mg to about 1 g per human patient per day). The amount of active compound that may be combined with the carrier materials to produce a single dosage form will vary depending upon the host treated and the particular mode of administration. Dosage unit forms will generally contain between from about 1 mg to about 500 mg of an active compound.

It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

As a consequence of its action in treating pathological conditions the compounds of the present invention posses utility for treatment of ungulate animals such as swine, cattle, sheep, and goats. The active compound of the invention can additionally be used for the treatment of household pets, for example companion animals such as dogs and cats. The administration of the active compounds of formula I can be effected orally or parenterally. An amount of the active compound of formula I is administered such that an effective dose is received, generally a daily dose which, when administered orally to an animal is usually between 0.01 and 20 mg/kg of body weight, preferably between 0.05 and 10 mg/kg of body weight. Conveniently, the medication can be carried in drinking water so that a therapeutic dosage of the agent is ingested with the daily water supply. The agent can be directly metered into drinking water, preferably in the form of a liquid, water-soluble concentrate (such as an aqueous solution of a water soluble salt).

Conveniently, the active compound can also be added directly to the feed, as such, or in the form of an animal feed supplement, also referred to as a premix or concentrate. A premix or concentrate of therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the active materials in the finished feed with which the premix is blended. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound according to the invention. The mixtures are thoroughly blended by standard procedures, such as in a twin shell blender, to ensure homogeneity.

If the supplement is used as a top dressing for the feed, it likewise helps to ensure uniformity of distribution of the active material across the top of the dressed feed.

Drinking water and feed effective for treating domestic animals are generally prepared by mixing the compound of the invention with a sufficient amount of animal feed to provide from about $10^{-3}$ to 500 ppm of the compound in the feed or water.

The preferred medicated swine, cattle, sheep and goat feeds generally contain from 1 to 400 grams of active compound per ton of feed, the optimum amount for these animals usually being about 50 to 300 grams per ton of feed.

The preferred poultry and domestic pet feeds usually contain about 1 to 400 grams and preferably 10 to 400 grams of active compound per ton of feed.

For parenteral administration in animals, the compounds of the present invention may be prepared in the form of a paste or a pellet and administered as an implant, usually under the skin of the head or ear of the animal in which increase in lean meat deposition and improvement in lean mean to fat ratio is sought.

In general, parenteral administration involves injection of a sufficient amount of the compound of the present invention to provide the animal with 0.01 to 20 mg/kg/day of body weight of the active ingredient. The preferred dosage for poultry, swine, cattle, sheep, goats and domestic pets is in the range of from 0.05 to 10 mg/kg/day of body weight of active ingredient.

What is claimed is:

1. A compound of the formula:

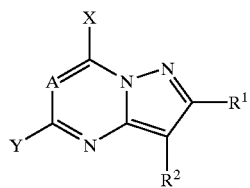

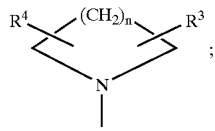

wherein X is
R$^1$ is phenyl, thienyl or pyridyl each optionally substituted with one to three substituents selected from halogen, —OCF$_3$, NO$_2$, CN, hydroxy, alkylalkoxy, COOH, C$_1$–C$_6$alkyl, C$_1$–C$_6$hydroxyalkyl, C$_1$–C$_6$ aminoalkyl, aryl, heteroaryl, alkoxy, acyloxy,

NR$^7$R$^8$, C$_1$–C$_4$alkylthio, mono-, di-, or trihaloalkyl, or
wherein R is phenyl, C$_1$–C$_6$alkyl, hydrogen, OH, or alkoxy;
R$^2$ is hydrogen or C$_1$–C$_6$alkyl;
R$^3$ and R$^4$ are independently hydrogen, hydroxyl, —N(C$_1$–C$_3$alkyl)$_2$, C$_1$–C$_6$alkyl, nitro, cyano, or alkylalkoxy, or aryloxy;
Y is hydrogen, C$_1$–C$_6$alkyl, or pyridyl;
n is 1 to 3;
m is 1 to 3; and
R$^7$ and R$^8$ are C$_1$–C$_6$ alkyl;
with the proviso that when n is 2. Y is hydrogen or C$_1$–C$_6$alkyl; and R$^3$ and R$^4$ are both hydrogen, then R$^1$ is not phenyl.

2. The compound of claim 1 wherein:
n is 2 or 3;
R$^3$ is —H or —OH$_3$;
R$^4$is —H;
Y is methyl;
R$^2$ is hydrogen; and
R$^1$ is 3-chlorophenyl, 4-chlorophenyl or thienyl.

3. The compound of claim 1 wherein:
n is2;
R$^3$ is H or methyl;
R$^4$ is H;
Y is methyl;
R$^1$ is halogenated phenyl, or trifluoro methoxyphenyl.

4. The compound of claim 1 selected from the group consisting of:
7-Azetidin-1-yl-5-methyl-2-phenyl-pyrazolo[1,5-a]pyrimidine;
2-Phenyl-5-pyridin-2-yl-7-pyrrolidin-1-yl-pyrazolo[1,5-a]pyrimidine;
5-Methyl-7-pyrrolidin-1-yl-2-thiophen-2-yl-pyrazolo[1,5-a]pyrimidine;
2-(3-Chloro-phenyl )-5-methyl-7-pyrrolidin-1-yl-pyrazolo[1,5-a]pyrimidine;
2-(4-Chloro-phenyl )-5-methyl-7-pyrrolidin-1-yl-pyrazolo[1,5-a]pyrimidine;
5-Methyl-7-pyrrolidin-1-yl-2-(4-trifluoromethoxy-phenyl )-pyrazolo[1,5-a]pyrimidine;
[4-(5-Methyl-7-pyrrolidin-1-yl-pyrazolo[1,5-a]pyrimidin-2-yl )-phenyl]-methanol;
2-(4-Chloro-phenyl )-5-methyl-7-(2-methyl-pyrrolidin-1-yl)-pyrazolo[1,5-a]pyrimidine;
2-(4-Chloro-phenyl)-5-methyl-7-piperidin-1-yl-pyrazolo[1,5-a]pyrimidine;
{1(S)-[2-(4-Chloro-phenyl )-5-methyl-pyrazolo[1,5-a]pyrimidin-7-yl]-pyrrolidin-3-yl}-dimethyl-amine;
{1(R)-[2-(4-Chloro-phenyl)-5-methyl-pyrazolo[1,5-a]pyrimidin-7-yl]-pyrrolidin-3-yl}-dimethyl-amine;
2-(4-Chloro-phenyl )-5-methyl-7-(2-methyl-piperidin-1-yl)-pyrazolo[1,5-a]pyrimidine;
1-[2-(4-Chloro-phenyl)-5-methyl-pyrazolo[1,5-a]pyrimidin-7-yl]-pyrrolidin-3-ol;
2-[4-(4-Ethyl-piperazin-1-ylmethyl)-phenyl]-5-methyl-7-pyrrolidin-1-yl-pyrazolo[1,5-a]pyrimidine; and
5-Methyl-2-pyridin-4-yl-7-pyrrolidin-1-yl-pyrazolo[1,5-a]pyrimidine.

5. A compound of claim 1 wherein one or more atoms are replaced by an atom having an atomic mass or mass number different from the atomic mass or mass number usually found in nature where said one or more atoms are selected from the group consisting of $^2$H, $^3$H, $^{13}$C, $^{14}$C, $^{15}$N, $^{18}$O, $^{17}$O, $^{35}$S, $^{18}$F, and $^{36}$Cl.

* * * * *